United States Patent [19]

Farb

[11] Patent Number: 5,366,968
[45] Date of Patent: Nov. 22, 1994

[54] MODULATION OF RECEPTOR-MEDIATED ION TRANSPORT

[75] Inventor: David H. Farb, Cambridge, Mass.

[73] Assignee: Trustees of Boston University, Boston, Mass.

[21] Appl. No.: 7,068

[22] Filed: Jan. 21, 1993

Related U.S. Application Data

[62] Division of Ser. No. 758,129, Sep. 12, 1991, Pat. No. 5,212,167.

[51] Int. Cl.$^5$ ............................................. A61K 31/56
[52] U.S. Cl. .................................... 514/178; 514/179; 514/182
[58] Field of Search ..................... 514/178, 179, 182

[56] References Cited

FOREIGN PATENT DOCUMENTS

89/02272 3/1989 WIPO .

OTHER PUBLICATIONS

Wu et al., "Inverse Modulation of γ-Aminobutyric Acid-Glycine-Induced Currents by Progesterone," *Molecular Pharmacology* 37:597–602 (1990).

Majewska et al., "Neurosteroid Pregnenolone Sulfate Antagonizes Electrophysiological Responses to GABA in Neurons," *Neuroscience Letters* 90:279–284 (1988).

Williams et al., "Modulation of the NMDA Receptor by Polyamines," *Life Sciences* 48:469–498 (1990).

Halliwell et al., "The Mechanism of Action and Pharmacological Specificity of the Anticonvulsant NMDA Antagonist MK-801: A Voltage Clamp Study on Neuronal Cells in Culture," *Br. J. Pharmacol.* 96:480–494 (1989).

Nowak et al., "Magnesium Gates Glutamate-Activated Channels in Mouse Central Neurones," *Nature* 307:462–465 (1984).

Johnson and Ascher, "Glycine Potentiates the NMDA Response in Cultured Mouse Brain Neurons," *Nature* 325:529–531 (1987).

Kleckner and Dingledine, "Requirement for Glycine in Activation of NMDA-Receptors Expressed in Xenopus Oocytes," *Science* 241:835–837 (1988).

Huettner, "Incole-2-Carbonxylic Acid: A Competitive Antagonist of Potentiation by Glycine at the NMDA Receptor," *Science* 243:1611–1613 (1989).

Kemp et al., "7-Cholorokynurenic Acid is a Selective Antagonist at the Glycine Modulatory Site of the N-Methyl-D-Aspartate Receptor Complex," *Neurobiology* 85:6547–6550 (1988).

Huettner and Bean, "Block of N-Methyl-D-Aspartate-Activated Current by the Anticonvulsant MK-801: Selective Binding to Open Channels," *Proc. Natl. Acad. Sci.* 85:1307–1311 (1988).

Rassendren, "Zinc Has Opposite Effects on NMDA and Non-NMDA Receptors Expressed in Xenopus Oocytes," *Neuron* 4:733–740 (1990).

Traynelis and Cull-Candy, "Proton Inhibition of N-methyl-D-Aspartate Receptors in Cerebellar Neurons," *Nature* 345:347–350 (1990).

Williams et al., "Effects of Polyamines on the Binding of [$^3$H]MK-801 to the N-Methyl-D-Aspartate Receptor: Pharmacological Evidence for the Existence of a Polyamine Recognition Site," *Molecular Pharmacology*, 36:575–581 (1989).

Lovinger et al., "Ethanol Inhibits NMDA-Activated Ion Current in Hippocampal Neurons," *Science* 243:1721–1724 (1989).

(List continued on next page.)

Primary Examiner—Marianne M. Cintins
Assistant Examiner—Kimberly R. Jordan
Attorney, Agent, or Firm—Hamilton, Brook, Smith & Reynolds

[57] ABSTRACT

The subject application discloses methods for modulating NMDA-mediated ion transport, and inhibiting non-NMDA glutamate-induced ion transport, in neuronal cells. The methods involve contacting a neuronal cell with an effective amount of the neurosteroid pregnenolone sulfate, or pharmacologically effective derivatives thereof.

11 Claims, 2 Drawing Sheets

OTHER PUBLICATIONS

McEwen, "Non-Genomic and Genomic Effects of Steroids on Neural Activity," *Tips Reviews* 12:141–146 (1991).

Majewska, "The Neurosteroid Dehydroepiandrosterone Sulfate is an Allosteric Antagonist of the $GABA_A$ Receptor," *Brain Research* 526:143–146 (1990).

Wu et al., "Pregnenolone Sulfate: A Positive Allosteric Modulator at the N-Methyl-D-Asparatate Receptor," *Mol. Pharmacol.* 40(3):333–336 (1991).

Spence et al., "The Neurosteroids Pregnenolone and Pregnenolone-Sulfate But Not Progesterone, Block Ca2+ Currents in Acutely Isolated Hippocampal CA1 Neurons," *Life Sci.* 49(26):235–239 (1991).

Irwin et al., "Pregnenolone Sulfate Augments NMDA Receptor Mediated Increases in Intracellular Ca2+ in Cultured Rat Hippolcampal Neurons," *Neurosci. Letters* 141(1):30–34 (1992).

Purdy et al., "Synthesis, Metabolism and Pharmacological Activity of 3Alpha-hydroxy Steroids which Potentiate GABA-Receptor-Mediated Chloride Ion Uptake in Rat Cerebral Cortical Synaptoneurosomes," *J. of Med. Chem.* 33(6):1576–1578 (1990).

Paul et al., "Neuroactive Steroids," *The FASEB J.* 6(6):2311–2333 (1992).

Demirgoren et al., "Receptor Binding and Electrophysiological Effects of Dehydroepiandrosterone Sulfate, and Antagonist of the GABAa Receptor," *Neurosci.* 45(1):127–135 (1991).

Callachan et al., "The Actions of the Steroidal Convulsant RU 5135 on Glycine and GABAa receptors," *British J. of Pharm.* 90:120 (1987).

MODULATION OF RECEPTOR-MEDIATED ION TRANSPORT

GOVERNMENT SUPPORT

Experimental work described herein was funded by National Institutes of Health Grants NS-23140 and NS-22116.

This application is a division of application Ser. No. 07/758,129 filed on Sep. 12, 1991, now U.S. Pat. No. 5,212,167.

BACKGROUND OF THE INVENTION

Neurotransmitters act through specific receptors and are responsible for regulating the conductance of ions (e.g., $K^+$, $Na^+$, $Cl^-$) across semi-permeable neuronal cell membranes. The active concentration of charged ions within a cell results in the establishment of an electrical potential across the membrane of the cell. A resting neuronal cell, for example, has a membrane potential of about $-80$ mv, the interior being negative with respect to the exterior of the cell. Neurotransmitters are stored in presynaptic vesicles and are released under the influence of neuronal action potentials. When released into the synaptic cleft, an excitatory chemical will generally cause membrane depolarization.

L-glutamate is thought to be the major excitatory neurotransmitter in the central nervous system. Two major pharmacological classes of glutamate-mediated ion channels have been identified. N-methyl-D-aspartate (NMDA) receptors respond preferentially to the synthetic analog of aspartate, N-methyl-D-aspartate, whereas non-NMDA receptors respond preferentially to kainate and α-amino-3-hydroxy-5-methyl-4-isoxazolepropionate (AMPA). Glutamate-induced NMDA receptors have attracted particular attention by virtue of their proposed role in long-term potentiation, learning, hypoxic neuronal damage, and epilepsy.

Although steroid effects mediated by genomic steroid response elements have been studied extensively, it is now evident that many steroids also have direct neuromodulatory effects on a variety of neurotransmitter receptors. Moreover, there is evidence for the local synthesis of certain steroids (termed "neurosteroids") in the brain. In particular, the neurosteroid pregnenolone sulfate (FIG. 1) has been proposed as an endogenous negative modulator of the GABA receptor in the brain. It has been previously shown that pregnenolone sulfate is a negative modulator of the glycine receptor.

SUMMARY OF THE INVENTION

The subject invention relates to the potentiation of glutamate-induced NMDA receptor-mediated ion transport and to the inhibition of γ-aminobutyric acid (GABA) and glycine receptor-mediated ion channel activity, across nerve cell membranes. This modulation is effected by contacting a nerve cell with pregnenolone sulfate (e.g., the α or β isomer or a mixture thereof). The invention also relates to the inhibition of glutamate-induced non-NMDA receptors. Derivatives of pregnenolone sulfate are also predicted to modulate ion transport. The invention also relates to agents, such as pregnenolone sulfate derivatives, which are useful in the present method.

Ion transport is known to play a profound role in cellular physiology, and the ability to selectively potentiate or inhibit the transport of ions across nerve cell membranes offers an opportunity for pharmacological intervention.

DETAILED DESCRIPTION OF THE INVENTION

Figure 1:
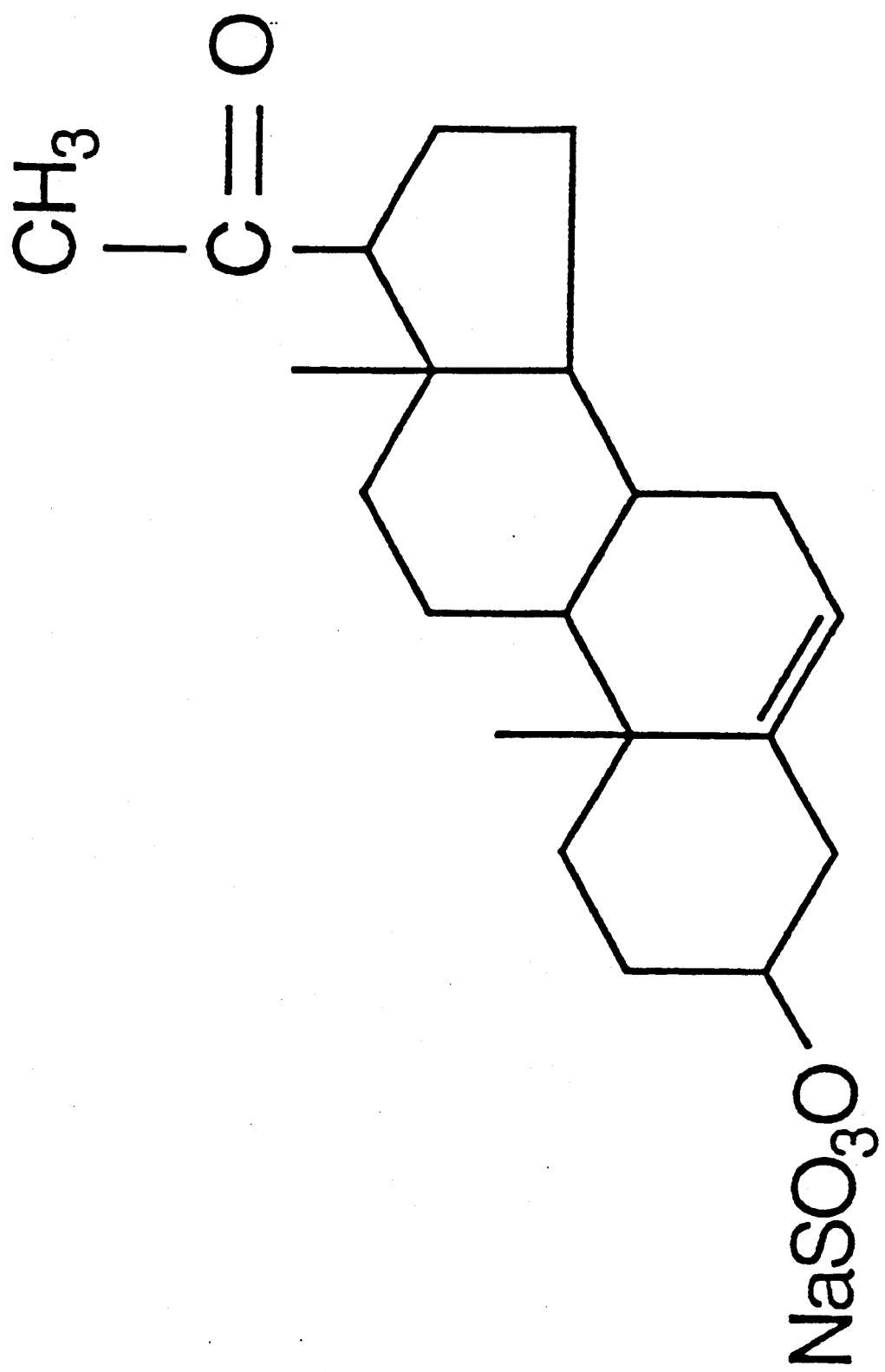
FIG. 1 is a diagram showing the general structure of pregnenolone sulfate.

The subject invention is based on the discovery that pregnenolone sulfate has a modulating effect on NMDA-mediated ion transport across nerve cell membranes. The general structure of pregnenolone sulfate is shown in FIG. 1. As described herein, when nerve cells are contacted with pregnenolone sulfate specifically, the glutamate-induced NMDA receptor-mediated response is specifically potentiated and the GABA and glycine-mediated responses are inhibited. Thus, contacting a nerve cell with the pregnenolone sulfate in an appropriate concentration, has been shown to result in a 3-fold increase in the ionic current across the cellular membrane. The effect of such treatment on glycine and GABA receptor-mediated in channel activity is a slight decrease. In addition, non-NMDA glutamate-induced activity is inhibited by pregnenolone sulfate.

The largest reported tissue concentrations of endogenous pregnenolone sulfate in the central nervous system are less than 1 μM (see e.g., Lanthier et al., *J. Steroid Biochem.* 25: 445–449 (1986) and Corpechot et al., *Brain Res.* 404: 355–360 (1987)). As is demonstrated in the Exemplification section below, this is below the concentration range at which the modulatory effect of pregnenolone sulfate on NMDA receptor-mediated neuronal ion channel activity was observed. Thus, to effect modulation of ion channel activity, a neuronal cell is contacted with pregnenolone sulfate, or an appropriate derivative thereof. Preferably, the concentration of pregnenolone sulfate is about 1–500 μM. A more preferred range is about 50–250 μM.

In addition to pregnenolone sulfate, one skilled in the art would predict with a high degree of certainty that derivatives of these compounds are also useful for modulating NMDA receptor-mediated ion channel activity. Those skilled in the art recognize that such modifications can increase the potency of a compound thereby resulting in activity at reduced concentrations. The term "potentiation" has been applied to this phenomenon. In addition, such modifications can have a positive effect on the delivery characteristics of a compound, resulting, for example, in an increased half-life when administered in vivo.

Such derivatives include, for example, derivatives in which the sulfate at position 3 of the steroid skeleton is replaced by an alkyl sulfate. The alkyl sulfates include, for example, methyl, ethyl, propyl, isopropyl and dimethyl sulfates.

Alternatively, pregnenolone sulfate derivatives in which the sulfate at position 3 of the steroid skeleton is replaced with an alkyl sulfonate can be used. These include, for example, methyl, ethyl, propyl, isopropyl and dimethyl sulfonates.

A third useful class of derivatives have an alkyl acetate in place of the sulfate at position 3. The alkyl acetates include, for example, methyl, ethyl, propyl, isopropyl and dimethyl acetates.

Any combination of the modifications described above, at positions 3, 5 and 6, would be expected to result in a compound useful for the stimulation of glutamate-induced NMDA receptor-mediated ion channel activity.

Another useful group of derivatives includes dehydroepiandrosterone sulfate, tetrahydrodeoxycorticosterone sulfate, allotetrahydrodeoxycorticosterone sulfate, 3α-hydroxy-5α-pregnane-11,20-dione sulfate (alfaxalone sulfate), alfadolone sulfate and 3α-hydroxy-16-imino-5β-17 aza-androstan-11-one sulfate.

EXEMPLIFICATION

The following experiments present data which demonstrates that NMDA-mediated ion transport across nerve cell membranes can be modulated by contacting the nerve cell with pregnenolone sulfate.

Cultures of dissociated spinal cord neurons were prepared from 7-day chick embryos as described by Wu et al. (*Mol. Pharmacol.* 37:597–602 (1990)). Briefly, dissociated cells were plated on collagen-coated 35-mm tissue culture dishes in Eagle's minimum essential medium supplemented with 2.4 mM glutamine, 10% (v/v) heat-inactivated horse serum, 5% (v/v) chick embryo extract, 100 units/ml penicillin, and 100 μg/ml streptomycin. Cultures were maintained in a humidified atmosphere of 5% $CO_2$/95% air at 37° C. Cytosine arabinoside (1 μM) was added after 36 hours to control the proliferation of non-neuronal cells. This medium was removed one day later and replaced with a similar medium supplemented with 20.5 mM glucose and 18 mM KCl, and containing 2.5% chick embryo extract. Fresh medium was added twice weekly. Cultured neurons were used in experiments 2–4 weeks after plating.

Electrophysiological experiments were carried out in 35-mm tissue culture dishes on the stage of an inverted phase-contrast microscope. Whole-cell currents were recorded by the whole-cell variant of the patch clamp technique described by Hamill et al. (*Pflugers Arch.* 391:85–100 (1981)). Patch electrodes were fabricated with a double pull from thin-wall borosilicate glass microcapillary pipets (Fischer) on a David Kopf vertical pipet puller (Model 700D). Electrode resistance was 5.2±0.12 MΩ (n=65) when filled with intracellular solution. The electrode solution usually contained (in mM): 10 KCl, 3 sodium gluconate, 140 potassium gluconate, 11 EGTA and 10 HEPES (pH adjusted to 7.2 with KOH). For GABA experiments, a high Cl-intracellular solution (in mM, 140 KCl, 3 NaCl, 1 $MgCl_2$, 11 EGTA and 10 HEPES, pH adjusted to 7.2 with KOH) was used. The bath solution contained (in mM): 150 NaCl, 4 KCl, 1 $CaCl_2$, 1 $MgCl_2$ and 10 HEPES (pH adjusted to 7.2 with NaOH). Since NMDA-induced currents are subject to voltage-dependent block by extracellular $Mg^{2+}$, no magnesium salts were added to the bath solution. All experiments were performed at room temperature (23°–25° C.).

Recordings were made using a Yale MK V amplifier. After forming a tight seal (typically 1–10 GΩ) capacitative transients were minimized. The patch of membrane under the pipet tip was then ruptured by gentle suction to obtain the whole-cell configuration. Cells with series resistance greater than 10 MΩ were rejected. Series resistance, which initially measured 7.3± 0.14 MΩ (n=65), was compensated (>60%). Only cells with resting membrane potential more negative than −55 mV and input resistance in excess of 150 MΩ were used. All recordings were made with the cell membrane potential clamped at −70 mV. Currents were filtered at 1 kHz using an 8-pole Bessel filter and digitized (40 ms/point) using an on-line data acquisition system (pClamp, Axon Instruments).

Drug solutions were applied to single neurons by pressure ejection (15 psi) from 7-barrel pipets (Choi et al., *J. Neurophysiol* 45:605–620 (1981) and Chan, C. Y. and D. H. Farb, *J. Neurosci.* 5:2365–2373 (1985)). Pipets were pulled from Omega dot tubing to a tip diameter of about 1 μm per barrel and broken back to about 3–5 μm per barrel after filling. Seven-barrel pressure pipets were positioned approximately 50 μm from the neuronal soma. Under these conditions, the drug solution in the pressure pipet rapidly and effectively replaces the solution surrounding the target neuron, with less than 10% dilution (Choi and Fischbach, *J. Neurophysiol.* 45:605–620 (1981)).

All drugs were obtained from Sigma, with the exception of AMPA hydrobromide (Research Biochemicals) and pregnenolone sodium sulfate (Steraloids). Stock solutions of steroids were prepared in dimethyl sulfoxide (final concentration, 0.5%, v/v). To obviate the possible effect of dimethyl sulfoxide on the relevant agonist-induced currents, all other drug solutions, including NMDA, kainate, AMPA, GABA, glycine and external buffer (in the pressure pipet), also contained 0.5% dimethyl sulfoxide. In all experiments, neurons received a 10 second pre-pulse of either external buffer or drug solution, followed by a 10 second application of agonist, followed by a 10–20 second pulse of external buffer solution. A period of 1–3 min was allowed between successive applications of agonist.

The degree of modulation of the amino acid response by pregnenolone sulfate, the percent change, is expressed as $(I'/I-1) \times 100\%$, where I is the average of control responses obtained from the same cell before application and after washout of pregnenolone sulfate, and I' is the agonist-induced current in the presence of pregnenolone sulfate. In all cases complete, or nearly complete, reversal of the steroid effect was obtained after washout. Throughout, results are expressed as mean±SEM; statistical comparison of groups was carried out using Student's t test.

Currents elicited by NMDA, kainate, AMPA, or GABA were recorded in primary cultures of chick spinal cord neurons by the whole-cell variant of the patch-clamp technique. At −70 mV, responses to 30 μM NMDA were increased approximately threefold by pregnenolone sulfate (100 μM). Enhancement of the NMDA response by pregnenolone sulfate was lower at 100 μM NMDA (86±7.5%, n=4), and virtually eliminated at 1 mM NMDA (1.3±1.3%, n=2). In contrast, responses elicited by kainate or AMPA were slightly inhibited by pregnenolone sulfate. The observation that AMPA- and kainate-induced currents are inhibited to the same extent by pregnenolone sulfate is consistent with the view that these two compounds activate the same receptor. Not all steroids enhance the response to NMDA. Hydrocortisone (100 μM) failed to enhance the NMDA-induced current, producing instead a slight (15±2.4%, n=6) inhibition of the NMDA response.

The response of the NMDA receptor is positively modulated by glycine and glycine may be an absolute requirement for receptor function. Because the glycine site associated with the NMDA receptor is of high affinity, it was important to verify that the enhancement produced by pregnenolone sulfate was not due to glycine contamination of the pregnenolone sulfate solution.

For this reason, the effect of pregnenolone sulfate on NMDA responses in the presence of a maximal concentration (10 μM) of glycine was examined. Potentiation of the NMDA response by pregnenolone sulfate did not differ significantly from the measured with out added glycine, indicating that glycine contamination cannot account for the observed effect.

The observation that pregnenolone sulfate potentiation of the NMDA response is unchanged in the presence of maximal glycine suggests that pregnenolone sulfate cannot act via the glycine modulatory site on the NMDA receptor, unless it does so with much greater efficacy than glycine itself. In the latter case, glycine should not be able to further enhance the NMDA response in the presence of a high concentration of pregnenolone sulfate. Electrochemical measurements also demonstrated that potentiation of the NMDA response by glycine (10 μM) was still evident in the presence of 100 μM of pregnenolone sulfate, indicating that the steroid modulatory site is distinct from the glycine modulatory site.

Figure 2:
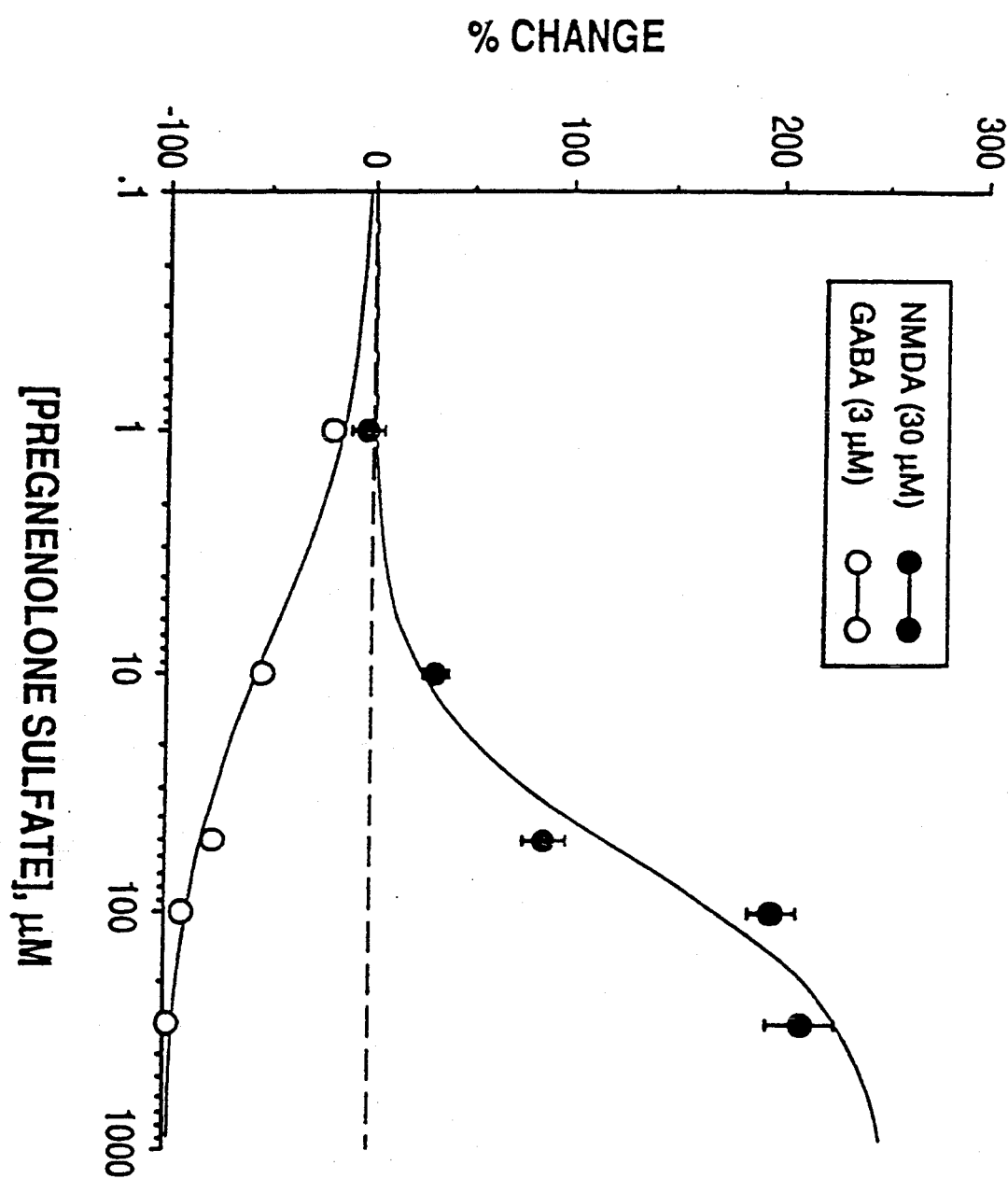
FIG. 2 is a diagram showing dose response curves for modulation of NMDA- and GABA-induced currents by pregnenolone sulfate.

FIG. 2 shows that enhancement of the NMDA response by pregnenolone sulfate was evident over roughly the same concentration range as inhibition of the GABA response, although pregnenolone sulfate was somewhat less potent at the NMDA receptor ($EC_{50}=57$ μM) than at the GABA receptor ($EC_{50}=7$ μM). In both cases, Hill slopes were close to 1, consistent with a single class of non-interacting sites. Although a full dose-response curve was not constructed for inhibition of the glycine response by pregnenolone sulfate, the response to 50 μM glycine was inhibited $61\pm2\%$ (n=6) by 5 μM pregnenolone sulfate, and $91\pm2\%$ (n=6) by 100 μM pregnenolone sulfate, suggesting that the potency of pregnenolone sulfate for inhibition of the glycine response is slightly greater than for inhibition of the GABA response.

EQUIVALENTS

Those skilled in the art will know, or be able to ascertain using no more than routine experimentation, many equivalents to the specific embodiments of the invention described herein. These and all other equivalents are intended to be encompassed by the following claims.

I claim:

1. A method for inhibiting non-NMDA glutamate receptor-mediated ion channel activity comprising contacting a neuronal cell with pregnenolone sulfate at a concentration of from about 1 to about 500 micromolar.

2. A method of claim 1 wherein the effective amount is a concentration of about 50–250 micromolar.

3. A method for inhibiting non-NMDA glutamate receptor-mediated ion channel activity in a neuronal cell comprising contacting the neuronal cell with a derivative of pregnenolone sulfate in which the sulfate at position 3 of the steroid skeleton is replaced by an alkyl sulfate, the concentration of the derivative of pregnenolone sulfate being from about 1 to about 500 micromolar.

4. A method of claim 3 wherein the alkyl sulfate is selected from the group consisting of methyl sulfates, ethyl sulfates, propyl sulfates, isopropyl sulfates and dimethyl sulfates.

5. A method for inhibiting non-NMDA glutamate receptor-mediated ion channel activity in a neuronal cell comprising contacting the neuronal cell with a derivative of pregnenolone sulfate in which the sulfate at position 3 of the steroid skeleton is replaced by an alkyl sulfonate, the concentration of the derivative of pregnenolone sulfate being from about 1 to about 500 micromolar.

6. A method of claim 5 wherein the alkyl sulfonate is selected from the group consisting of methyl sulfonates, ethyl sulfonates, propyl sulfonates, isopropyl sulfonates and dimethyl sulfonates.

7. A method for inhibiting non-NMDA glutamate receptor-mediated ion channel activity in a neuronal cell comprising contacting the neuronal cell with a derivative of pregnenolone sulfate in which the sulfate at position 3 of the steroid skeleton is replaced by an alkyl acetate, the concentration of the derivative of pregnenolone sulfate being from about 1 to about 500 micromolar.

8. A method of claim 7 wherein the alkyl sulfonate is selected from the group consisting of methyl acetates, ethyl acetates, propyl acetates, isopropyl acetates and dimethyl acetates.

9. A method for inhibiting non-NMDA glutamate receptor-mediated ion channel activity in a neuronal cell comprising contacting the neuronal cell with a derivative of pregnenolone sulfate in which the steroid skeleton is modified to add the subistituents selected from the group consisting of 5,6 dihydro, 5 hydroxy, 6 hydroxy, 5 methyl and 6 methyl, the concentration of the derivative of pregnenolone sulfate being from about 1 to about 500 micromolar.

10. A method for inhibiting non-NMDA glutamate receptor-mediated ion channel activity in a neuronal cell comprising contacting the neuronal cell with a derivative of pregnenolone sulfate having modifications selected from the group consisting of:
   a) substitution of the sulfate at position 3 of the steroid skeleton with a chemical group selected from the group consisting of alkyl sulfates, alky sulfonates and alkyl acetates;
   b) additions at position 5 of the steroid skeleton with a chemical group selected from the group consisting of dihydro, hydroxy and methyl;
   c) additions at position 6 of the steroid skeleton with a chemical group selected from the group consisting of dihydro, hydroxy and methyl, the concentration of the derivative of pregnenolone sulfate being from about 1 to about 500 micromolar.

11. A method for inhibiting non-NMDA glutamate receptor-mediated ion channel activity in a neuronal cell comprising contacting the neuronal cell with a pregnenolone sulfate derivative selected from the group consisting of dehydroepiandrosterone sulfate, tetrahydrodeoxycorticosterone sulfate, allotetrahydrodeoxycorticosterone sulfate, 3α-hydroxy-5α-pregnane-11,20-dione sulfate alfadolone sulfate and 3α-hydroxy-16-imino-5α-17 aza-androstan-11-one sulfate, the concentration of the derivative of pregnenolone sulfate being from about 1 to about 500 micromolar.

* * * * *

UNITED STATES PATENT AND TRADEMARK OFFICE
CERTIFICATE OF CORRECTION

PATENT NO. : 5,366,968
DATED : November 22, 1994
INVENTOR(S) : David H. Farb

It is certified that error appears in the above-indentified patent and that said Letters Patent is hereby corrected as shown below:

Column 6, Claim 10, line 39 after "sulfate" insert
--the concentration of the derivative of pregnenolone sulfate being from about 1 to about 500 micromolar--.

Column 6, Claim 10, line 50: delete ", the concentration of the derivative of pregnenolone sulfate being from about 1 to about 500 micromolar".

Column 6, Claim 11, line 61: delete "α" and insert --β--.

Signed and Sealed this

Twenty-first Day of March, 1995

Attest:

BRUCE LEHMAN

Attesting Officer

Commissioner of Patents and Trademarks